(12) United States Patent
Mangat et al.

(10) Patent No.: US 10,231,624 B2
(45) Date of Patent: Mar. 19, 2019

(54) INTRA-OPERATIVE HEAD AND NECK NERVE MAPPING

(75) Inventors: Gurpreet Mangat, Markham (CA); Lukasz Brzozowski, Mississauga (CA)

(73) Assignee: NOVADAQ TECHNOLOGIES ULC, Burnaby BC (CA)

( * ) Notice: Subject to any disclaimer, the term of this patent is extended or adjusted under 35 U.S.C. 154(b) by 2395 days.

(21) Appl. No.: 12/063,349

(22) PCT Filed: Aug. 10, 2006

(86) PCT No.: PCT/CA2006/001317
§ 371 (c)(1),
(2), (4) Date: May 12, 2010

(87) PCT Pub. No.: WO2007/016790
PCT Pub. Date: Feb. 15, 2007

(65) Prior Publication Data
US 2010/0222673 A1 Sep. 2, 2010

Related U.S. Application Data

(60) Provisional application No. 60/707,568, filed on Aug. 10, 2005.

(51) Int. Cl.
| | | |
|---|---|---|
| *A61B 5/05* | (2006.01) | |
| *A61B 5/00* | (2006.01) | |
| *A61K 49/00* | (2006.01) | |
| *A61B 90/00* | (2016.01) | |

(52) U.S. Cl.
CPC ............ *A61B 5/0059* (2013.01); *A61B 5/415* (2013.01); *A61B 5/418* (2013.01); *A61B 5/4893* (2013.01); *A61K 49/0034* (2013.01); *A61B 90/04* (2016.02)

(58) Field of Classification Search
USPC .......................... 600/431, 439, 427, 473, 476
See application file for complete search history.

(56) References Cited

U.S. PATENT DOCUMENTS

| | | | |
|---|---|---|---|
| 5,279,298 A | 1/1994 | Flower | |
| 5,438,989 A | 8/1995 | Hochman et al. | |
| 5,465,718 A | 11/1995 | Hochman et al. | |
| 5,496,369 A * | 3/1996 | Howard, III | .......... 623/10 |
| 5,519,534 A * | 5/1996 | Smith et al. | ........... 359/599 |
| 5,699,798 A | 12/1997 | Hochman et al. | |
| 6,149,671 A | 11/2000 | Nordquist et al. | |
| 6,196,226 B1 | 3/2001 | Hochman et al. | |
| 6,233,480 B1 | 5/2001 | Hochman et al. | |
| 6,241,672 B1 | 6/2001 | Hochman et al. | |

(Continued)

FOREIGN PATENT DOCUMENTS

| | | |
|---|---|---|
| JP | 3896176 | 12/1997 |
| WO | WO 93/25141 | 12/1993 |
| WO | WO 2005/034747 | 4/2005 |

OTHER PUBLICATIONS

Angelov et at., "Contralateral trigeminal nerve lesion reduces polyneuronal muscle innervation after facial nerve repair in rats", Eur. J. Neurosci., 11:1369-1378 (1999).

(Continued)

*Primary Examiner* — Joel F Brutus
(74) *Attorney, Agent, or Firm* — Oliff PLC

(57) ABSTRACT

The invention provides both systems and kits for medical imaging of nerves in the head and neck of a subject.

22 Claims, 1 Drawing Sheet

(56) References Cited

U.S. PATENT DOCUMENTS

| | | |
|---|---|---|
| 6,331,703 B1 | 12/2001 | Yarnall et al. |
| 6,335,429 B1 | 1/2002 | Cai et al. |
| 6,351,663 B1 | 2/2002 | Flower et al. |
| 6,485,413 B1* | 11/2002 | Boppart et al. ............... 600/160 |
| 6,671,540 B1* | 12/2003 | Hochman ..................... 600/431 |
| 6,804,549 B2 | 10/2004 | Hayashi |
| 6,821,946 B2 | 11/2004 | Goldsaink et al. |
| 6,853,857 B2 | 2/2005 | Pfeiffer et al. |
| 6,899,675 B2 | 5/2005 | Cline et al. |
| 6,915,154 B1 | 7/2005 | Docherty |
| 7,381,400 B2 | 6/2008 | Woltering |
| 2002/0146369 A1 | 10/2002 | Goldenberg |
| 2003/0156252 A1 | 8/2003 | Morris |
| 2003/0187349 A1 | 10/2003 | Kaneko et al. |
| 2003/0232016 A1 | 12/2003 | Heinrich |
| 2003/0236458 A1 | 12/2003 | Hochman |
| 2004/0109231 A1 | 6/2004 | Haisch et al. |
| 2004/0156782 A1 | 8/2004 | Alam et al. |
| 2004/0171827 A1* | 9/2004 | Peng et al. .................... 540/145 |
| 2004/0174495 A1 | 9/2004 | Levine |
| 2004/0206364 A1 | 10/2004 | Flower |
| 2005/0069525 A1 | 3/2005 | Mikael |
| 2005/0107380 A1 | 5/2005 | Nimmo et al. |
| 2005/0182321 A1 | 8/2005 | Frangioni et al. |
| 2005/0197583 A1 | 9/2005 | Chance |
| 2006/0013768 A1 | 1/2006 | Woltering |
| 2006/0108509 A1 | 5/2006 | Frangioni et al. |
| 2006/0241499 A1 | 10/2006 | Irion et al. |
| 2007/0203413 A1 | 8/2007 | Frangioni |

OTHER PUBLICATIONS

Komurcu et al., "Management strategies for peripheral iatrogenic nerve lesions", Annals of Plastic Surgery, 54 (2):135-139 (2005).

Akintunde et al., "Quadruple labeling of brain-stem neurons: a multiple retrograde fluorescent tracer study of axonal collateralization," Journal of Neuroscience Methods, 45:15-22, (1992).

Butter et al., "Melanoma in children and the use of sentinel lymph node biopsy," Journal of Pediatric Surgery, 40:797-800, (2005).

Dail et al., "Multiple vasodilator pathways from the pelvic plexus to the penis of the rat," International Journal of Impotence Research, 11:277-285, (1999).

Dan et al., "1% Lymphazurin vs 10% Fluorescein for Sentinel Node Mapping in Colorectal Tumors," Arch Surg, 139:1180-1184, (2004).

Degrand et al., "An Operational Near-Infrared Fluorescence Imaging System Prototype for Large Animal Surgery," Technology in Cancer Research & Treatment, 2(6):1-10, (2003).

Demos, "Near-infrared autofluorescence imaging for detection of cancer," Journal of Biomedical Optics, 9(3):587-592, (2004).

Dietz et al., "Indocyanine Green, Evidence of Neurotoxicity in Spinal Root Axons," Anesthesiology, 98(2):516-520, (2003).

Dunne et al., "Value of sentinel lymphonodectomy in head and neck cancer patients without evidence of lymphogenic metastatic disease," Auris Nasus Larynx, 28:339-344, (2001).

Frangioni "In vivo near-infrared fluorescence imaging," Current Opinion in Chemical Biology, 7:626-634, (2003).

Fritzsch et al., "Sequential double labeling with different fluorescent dyes coupled to dextran amines as a tool to estimate the accuracy of tracer application and of regeneration," Journal of Neuroscience Methods, 39:9-17, (1991).

Gipponi et al., New Fields of Application of the Sentinel Lymph Node Biopsy in the Pathologic Staging of Solid Neoplasms: Review of Literature and Surgical Perspectives, 85:171-179, (2004).

Glover et al., "Fluorescent dextran-amines used as axonal tracers in the nervous system of the chicken embryo," Journal of Neuroscience Methods, 18:243-254, (1986).

Haglund et al., "Enhanced Optical Imaging of Rat Gliomas and Tumor Margins," Neurosurgery, 35(5):930-941, (1994).

Haglund et al., "Enhanced Optical Imaging of Human Gliomas and Tumor Margins," Neurosurgery, 38(2):308-317, (1996).

Humblet et al., "High-affinity Near-infrared Fluorescent Small-molecule Contrast Agents for In Vivo Imaging of Prostate-specific Membrane Antigen," Molecular Imaging, 4(4):448-462, (2005).

Jamis-Dow, et al., "Small (≤3-cm) Renal Masses: Detection with CT versus US and Pathologic Correlation," Radiology, 198(3):785-788, (1996).

Kamolz et al., "Indocyanine green video angiographies help to identify burns requiring operation," Burns, 29:785-791, (2003).

Kim et al., "Near-infrared fluorescent type II quantum dots for sentinel lymph node mapping," Nature Biotechnology, 22(1):93-97, (2004).

Kobbert et al., "Current concepts in neuroanatomical tracing," Progress in Neurobiology, 62:327-351, (2000).

Lanciego et al., "Multiple axonal tracing: simultaneous detection of three tracers in the same section," Histochem Cell Biol, 110:509-515, (1998).

Lanciego et al., "Multiple neuroanatomical tracing in primates," Brain Research Protocols, 2:323-332, (1998).

Liedberg et al., "Intraoperative Sentinel Node Detection Improves Nodal Staging in Invasive Bladder Cancer," The Journal of Urology, 175:84-89, (2006).

Liedberg et al., Sentinel-Node-Diagnostik beim invasiven (Bladder Cancer and the Sentinel Node Concept), Aktuel Urol, 34:115-118, (2003).

Liptay, "Sentinel Node Mapping in Lung Cancer," Annals of Surgical Oncology, 11(3):271S-274S, (2004).

Malmstrom et al., "Early Metastatic Progression of Bladder Carcinoma: Molecular Profile of Primary Tumor and Sentinel Lymph Node," The Journal of Urology, 168:2240-2244, (2002).

Marangos et al., "In vivo visualization of the cochlear nerve and nuclei with fluorescent axonal tracers," Hearing Research, 162:48-52, (2001).

Minciacchi et al., "A procedure for the simultaneous visualization of two anterograde and different retrograde fluorescent tracers," Journal of Neuroscience Methods, 38:183-191, (1991).

Motomura et al. "Sentinel Node Biopsy Guided by Indocyanin Green Dye in Breast Cancer Patients," Jpn J Clin Oncol, 29(12):604-607, (1999).

Nimura et al., "Infrared ray electronic endoscopy combined with indocyanine green injection for detection of sentinel nodes of patients with gastric cancer," British Journal of Surgery, 91:575-579, (2004).

Paques et al., "Axon-Tracing Properties of Indocyanine Green," Arch Ophthalmol, 121:367-370, (2003).

Parungo et al., "Intraoperative identification of esophageal sentinel lymph nodes with near-infrared fluorescence imaging," The Journal of Thoracic and Cardiovascular Surgery, 129(4):844-850, (2005).

Puigdellivol-Sanchez et al., "On the use of fast blue, fluoro-gold and diamidino yellow for retrograde tracing after peripheral nerve injury: uptake, fading, dye interactions, and toxicity," Journal of Neuroscience Methods, 115:115-127, (2002).

Raabe et al., "Near-Infrared Indocyanine Green Video Angiography: A New Method for Intraoperative Assessment of Vascular Flow," Neurosurgery, 52(1):132-139, (2003).

Ross et al., "Sentinel Node Biopsy in Head and Neck Cancer: Preliminary Results of a Multicenter Trial," Annals of Surgical Oncology, 11(7):690-696, (2004).

Ross et al., "The ability of lymphoscintigraphy to direct sentinel node biopsy in the clinically no neck for patients with head and neck squamous cell carcinoma," The British Journal of Radiology, 75:950-958, (2002).

Rubben et al., "Infrared Videoangiofluorography of the Skin with Indocyanine Green-Rat Random Cutaneous Flap Model and Results in Man," Microvascular Research, 47:240-251, (1994).

Schmued et al., "In vivo anterograde and retrograde axonal transport of the fluorescent rhodamine-dextran-amine, Fluoro-Ruby, within the CNS," Brain Research, 526:127-134, (1990).

Sherif et al., "Lymphatic Mapping and Detection of Sentinel Nodes in Patients with Bladder Cancer," The Journal of Urology, 166:812-815, (2001).

(56) References Cited

OTHER PUBLICATIONS

Shoaib et al., "The Accuracy of Head and Neck Carcinoma Sentinel Lymph Node Biopsy in the Clinically no Neck," 5$^{th}$ International Conference on Head and Neck Cancer, San Francisco, CA, pp. 2077-2083, (2001).
Soltesz et at, "Intraoperative Sentinel Lymph Node Mapping of the Lung Using Near-Infrared Fluorescent Quantum Dots," Ann Thorac Surg 79:269-277, (2005).
Stoeckli et al., "Sentinel lymph node evaluation in squamous cell carcinoma of the head and neck," 5$^{th}$ International Conference on Head and Neck Cancer, pp. 221-226, Jul. 29-Aug. 3, 2000.
Sugi et al., "Comparison of three tracers for detecting sentinel lymph nodes in patients with clinical no lung cancer," Lung Cancer, 39:37-40, (2003).
Tubbs et al., "Anatomic Landmarks for Nerves of the Neck: A Vade mecum for Neurosurgeons," Neurosurgery, 56:ON5256-ON5260, (2005).
Uren, "Cancer surgery joins the dots," Nature Biotechnology, 22(1):38-39, (2004).
Valero-Cabre et al., "Superior Muscle Reinnervation After Autologous Nerve Graft or Poly-L-Lactide-ϵ-Caprolactone (PLC) Tube Implantation in Comparison to Silicone Tube Repair," Journal of Neuroscience Research, 63:214-223, (2001).
Oddi et al., "Intraoperative Biliary Tree Imaging with Cholyl-Lysyl-Fluorescein: An Experimental Study in the rabbit" Surgical Laparoscopy & Endoscopy 6(3):198-200 (1996).
Ohnishi et al., "Organic Alternatives to Quantum Dots for Intraoperative near-Infrared Fluorescent Lymph Node Mapping" Molecular Imaging, 4(3):172-181 (2005).
Kurihara et al., "Nerve Staining with Leucomethylene Blue: An Experimental Study," Plastic and Reconstruction Surgery 73(6):960-964 (1984).
Nahlieli et al., "Intravital Staining with Methylene Blue as an Aid to Facial Nerve Identification in Parotid Gland Surgery" J. Oral Maxillofac. Surgery 59:355-356 (2001).

Author Unknown, "Invitrogen," Material Safety Data Sheet, Jun. 4, 2008, p. 1-4.
Schmued et al., "Intracranial Injection of Fluoro-Gold Results in the Degeneration of Local but not Retrogradely Labeled Neurons," Brain Research, 626:71-77 (1993).
Naumann et al., "Retrograde Tracing of Fluoro-Gold: Different Methods of Tracer Detection at the Ultrastructural Level and Neurodegenerative Changes of Back-Filled Neurons in Long-Term Studies," Journal of Neuroscience Methods, 103:11-21 (2000).
He, "Fluorogold Induces Persistent Neurological Deficits and Circling Behavior in Mice Over-Expressing Human Mutant Tau," Current Neurovascular Research 6:54-61 (2009).
Garrett et al., "Fluoro-Gold's Toxicity Makes It Inferior to True Blue for Long-Term Studies of Dorsal Root Ganglion Neurons and Motoneurons," Neuroscience Letters 128:137-139 (1991).
Leissner et al., "Extended Radical Lymphadenectomy in patients with urothelial bladder cancer: Results of a prospective multicenter study," J. of Urol. 171:139-144 (2004).
Malmstrom et al. "RE: Extended radical lymphadenectomy in patients with urothelial bladder cancer: Results of a prospective multicenter study," J. of Urol. 172:386-386 (2004).
Nakayama et al., "Functional near-infrared fluorescence imaging for cardiac surgery and targeted gene therapy," Molecular Imaging, 1(4):365-377 (2002).
Parungo et al, "In vivo optical imaging of pleural space drainage to lymph nodes of prognostic significance," Annals of Surgical Oncology, 11(12):1085-1092 (2004).
Schneider et al., "Fluorescence of testicle. An indication of viability of spermatic cord after torsion," Urology, 5(1):133-136 (1975).
U.S. Appl. No. 11/851,312, filed Sep. 6, 2007 in the name of Golijanin et al.
U.S. Appl. No. 11/515,419, filed Sep. 1, 2006 in the name of Golijanin et al.

* cited by examiner

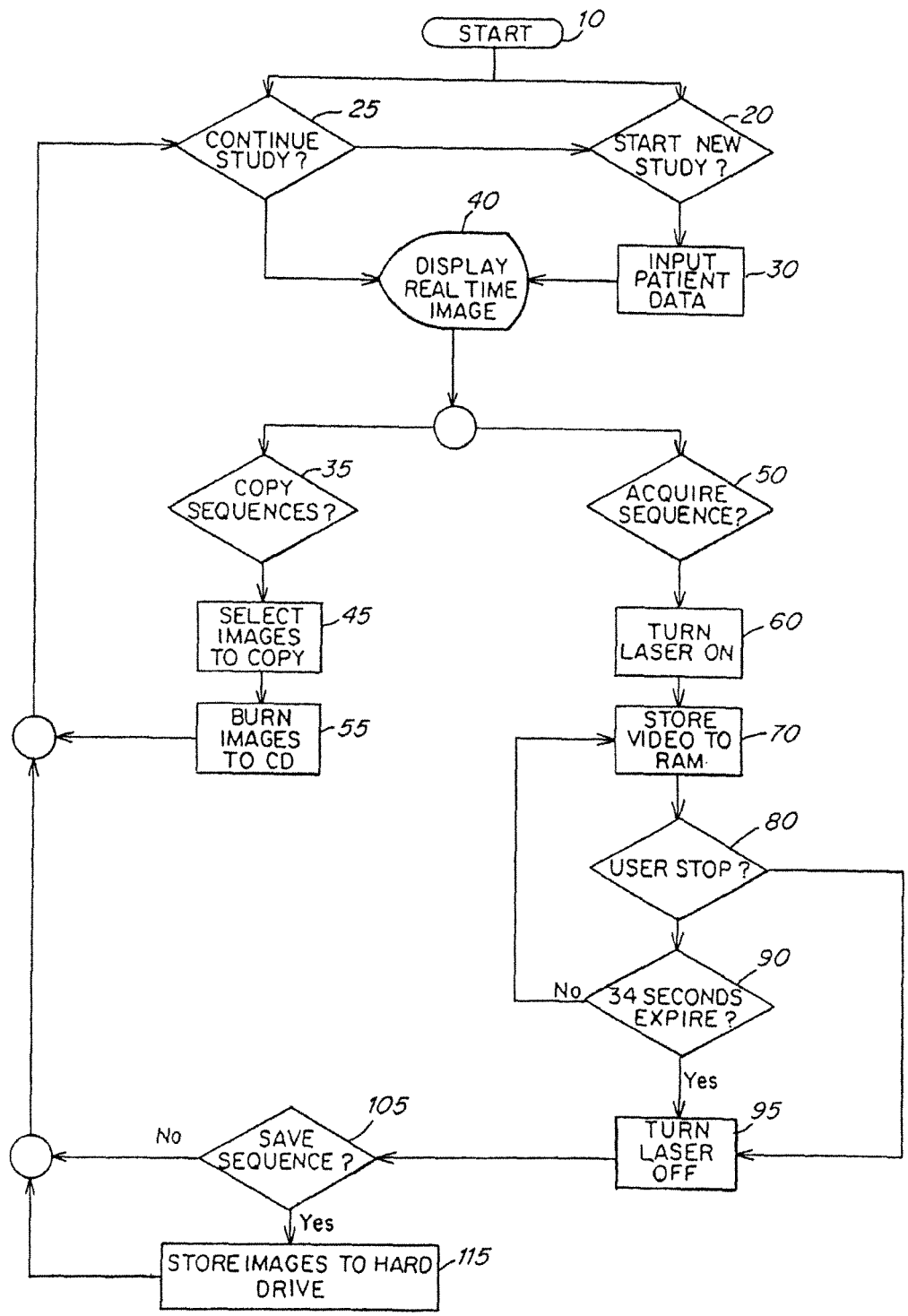

# INTRA-OPERATIVE HEAD AND NECK NERVE MAPPING

RELATED APPLICATIONS

This application is a National Stage Application of PCT/CA2006/001317, filed Aug. 10, 2006, which claims the benefit of U.S. Provisional Application Ser. No. 60/707,568, filed Aug. 10, 2005, the disclosures of all of which are incorporated herein by reference in their entirety as if fully set forth herein.

FIELD OF THE INVENTION

The invention relates generally to the field of medical imaging. Methods are provided for intra-operatively imaging one or more nerves in a subject for the purpose of avoiding iatrogenic nerve injury. In certain embodiments, methods are also provided for imaging sentinel lymph nodes (SLN) in the head and neck. Certain other embodiments provide kits that are useful for carrying out methods of the invention.

BACKGROUND OF THE INVENTION

It is well known that nerve injury due to iatrogenesis can result in debilitating loss of function to the subject. Common causes of iatrogenic nerve injury include surgical failure, traction or pressure lesions, hematoma, or inadequate positioning of the subject (Fercan Komurcu, MD et al., 2005, Annals of Plastic Surgery, 54(2):135-139).

Iatrogenic injury to head or neck nerves can be particularly serious since the head and neck house nerves involved in important bodily functions. For example, the facial nerve is the most frequently injured nerve in the head or neck area. Most facial nerve lesions are postoperative and result in loss of facial tone, voluntary movement and emotional expression in the face. Prognosis remains poor even after the use of all available microsurgical techniques to repair the injured nerve (Doychin N. Angelov et al., 1999, European Journal of Neuroscience, Vol. II., 1369-1378).

As another example, ProNational Insurance Company, a provider of medical liability insurance, frequently sees claims alleging injury to the 11th cranial (spinal accessory) nerve associated with posterior cervical node excision. Such injury results in partial or total paralysis of the sternocleidomastoid and the upper trapezius muscles. Additional symptoms often include winging of the scapula and sagging and weakness of the shoulder. (Harvey Gass, M.D., and Lizabeth F. Brott, J.D., "Practice Protection, Claims Review. 11th Nerve Injury With Posterior Cervical Node Excision", 2001, published at http://www.pronational.com/news/advisor/Pratpro1Q2001.htm).

Efforts have focused on repairing nerve injury. For example, U.S. Patent Publications 20050069525 and 20050107380, and U.S. Pat. No. 6,821,946 each disclose methods and/or compounds for ameliorating nerve injury. However, nerve repair often does not lead to full recovery, and prognosis is often poor (see e.g., Doychin N. Angelov et al., supra).

Others have attempted to prevent iatrogenic nerve injury by educating surgeons. For example, R. Shane Tubbs, M.S., P.A.-C., Ph.D., et al. compiled information about anatomical landmarks useful for locating nerves in the head or neck (see, e.g., R. Shane Tubbs, M.S., P.A.-C., Ph.D., et al., Neurosurgery 56[ONS Suppl 2]:ONS-256-ONS-260, 2005). However, literature can only provide generalized anatomical information. Minute anatomical differences exist between all individuals. A surgical team cannot determine a particular nerve's exact position or path in a particular individual simply by reading generalized anatomical literature.

There is thus a need for improved methods of preventing iatrogenic nerve injury, particularly in the head and neck area. In addition, there is a need for improved technology to provide a surgical team with definitive information about the location of nerves in individual subjects.

SUMMARY OF THE INVENTION

In certain embodiments, the invention provides a method of reducing the risk of iatrogenic nerve injury during a surgical procedure of the subject's head or neck. This method includes the steps of (a) administering a first fluorescent dye to a subject, (b) applying a sufficient amount of energy to the subject's head or neck such that the fluorescent dye fluoresces, (c) intra-operatively obtaining a fluorescent image of at least a portion of the subject's head or neck, and (d) observing the fluorescent image to determine the presence or absence of at least one nerve in the fluorescent image.

In certain other embodiments, the invention provides a kit for reducing the risk of iatrogenic nerve injury to a subject during a surgical procedure of the head or neck. The kit includes a first fluorescent dye and instructions to: (a) administer the first fluorescent dye to the subject, (b) apply a sufficient amount of energy to the subject's head or neck such that the fluorescent dye fluoresces, (c) intra-operatively obtain a fluorescent image of at least a portion of the subject's head or neck, and (d) observe the fluorescent image to determine the presence or absence of at least one nerve in the fluorescent image.

BRIEF DESCRIPTION OF THE DRAWINGS

The above and further advantages of the invention may be better understood by referring to the following description in conjunction with the accompanying drawing in which:

FIG. 1 illustrates imaging software that may be used in certain embodiments of the invention.

DETAILED DESCRIPTION

Definitions

"At least a portion" means either less than the entirety or the entirety thereof.

A "computer" as used herein refers to a conventional computer as understood by the skilled artisan. For example, a computer generally includes a central processing unit that may be implemented with a conventional microprocessor, a random access memory (RAM) for temporary storage of information, and a read only memory (ROM) for permanent storage of information. A memory controller is provided for controlling RAM. A bus interconnects the components of the computer system. A bus controller is provided for controlling the bus. An interrupt controller is used for receiving and processing various interrupt signals from the system components. Mass storage may be provided by diskette, CD ROM or hard drive. Data and software may be exchanged with computer system via removable media such as the diskette or CD ROM. A CD ROM drive is connected to the bus by the controller. The hard disk is part of a fixed disk drive that is connected to the bus by a controller. User input to the computer may be provided by a number of devices. For example, a keyboard and mouse may be connected to the bus by a controller. An audio transducer that might act as both a microphone and a speaker may be connected to the bus by an audio controller. It will be obvious to those reasonably skilled in the art that other input devices, such as a pen and/or tablet may be connected to the bus and an appropriate controller and software, as required. A visual display can be generated by a video controller that controls a video display. Preferably, the computer further includes a network interface that allows the system to be interconnected to a local area network (LAN) or a wide area network (WAN). Operation of the computer is generally controlled and coordinated by operating system software, such as the Solaris operating system, commercially available from Sun Microsystems, the UNIX® operating system, commercially available from The Open Group, Cambridge, Mass., the OS/2® operating system, commercially available from International Business Machines Corporation, Boca Raton, Fla., or the Windows NT operating system, commercially available from MicroSoft Corp., Redmond, Wash. The operating system controls allocation of system resources and performs tasks such as processing scheduling, memory management, networking, and I/O services, among things. In particular, an operating system resident in system memory and running on the CPU coordinates the operation of the other elements of computer.

As used herein, the term "patient" is synonymous with "subject" as defined below.

"Subject" as used herein, refers to any animal. The animal may be a mammal. Examples of suitable mammals include, but are not limited to, humans, non-human primates, dogs, cats, sheep, cows, pigs, horses, mice, rats, rabbits, and guinea pigs.

Description

Surgical procedures of the head and neck can lead to iatrogenic nerve injury. In certain embodiments the invention seeks to reduce such risks by providing methods which permit the surgeon to intra-operatively locate the position of the nerves in the area(s) on which surgery is to be performed or is being performed. In certain embodiments the methods of the invention may also be used to determine the position of sentinel lymph nodes in the head and neck.

Kits are further provided for carrying out various methods of the invention.

Methods of the Invention

In certain embodiments the invention provides a method for imaging at least one nerve in the head or neck of a subject. The image may be obtained intra-operatively. Thus the area where surgery is to be performed or nearby regions may be surgically exposed.

The method comprises: (a) administering a first fluorescent dye to a subject, (b) applying a sufficient amount of energy to the subject's head or neck such that the fluorescent dye fluoresces, (c) intra-operatively obtaining a fluorescent image of at least a portion of the subject's head or neck, and (d) observing the fluorescent image to determine the presence or absence of at least one nerve in the fluorescent image. The fluorescent dye is administered at least about an hour before at least a portion of the head or neck is exposed to a form of radiant energy as described herein. Other suitable administration time ranges within the scope of the invention include: between about one hour and about one day, between about one hour and about five days, between about one hour and about 10 days, between about one hour and about twenty days, between about one hour and about twenty-five days, between about one hour and about thirty days, between about one hour and about sixty days before the exposure described herein.

Thus, by observing the fluorescent image the surgical team can determine the absence or presence of a nerve in the image. Nerves may be identified by their size, shape, gross location and/or fluorescent dye signature. The surgical team may further determine the location of one or more specific nerve(s) by observing the image. The surgical team can thus use information about the presence/absence or location of one or more nerves to determine how they will perform the surgical procedure. For example, based on information obtained through use of the methods, the surgical team may decide to make an incision at a point on the subject's head or neck where they are relatively less likely to inadvertently cut or surgically contact a particular nerve.

Any nerve in the head or neck can be imaged with the methods described herein. Examples of nerves in the head or neck that can be imaged include: (a) Abducens, (b) Ansa Cervicales, (c) Anterior Ethmoidal, (d) Auriculotemporal, (e) Buccal, (f) Chorda Tympani, (g) Deep Petrosal Nerve, (h) External Laryngeal, (i) External Nasal, (j) Facial, (k) Frontal, (l) Glossopharyngeal, (m) Great Auricular, (n) Greater Occipital, (o) Greater Petrosal, (p) Hypoglossal, (q) Inferior Alveolar, (r) Infraorbital, (s) Infratrochlear, (t) Internal Laryngeal, (u) Internal Nasal Medial, (v) Internal Nasal Lateral, (w) Lacrimal, (x) Lesser Occipital, (y) Lesser Petrosal, (z) Lingual, (aa) Long Ciliary, (ab) Mandibular, (ac) Maxillary, (ad) Mental, (ae) Nasociliary, (af) Nasopalatine, (ag) Oculomotor, (ah) Olfactory, (ai) Ophthalmic, (aj) Optic, (ak) Palatine Greater, (al) Palatine Lesser, (am) Pharyngeal, (an) Phrenic, (ao) Recurrent Laryngeal, (ap) Short Ciliary, (aq) Spinal Accessory, (ar) Superior Alveolar, (as) Superior Laryngeal, (at) Supraorbital, (au) Supratrochlear, (av) Supraclavicular, (aw) Transverse Cervical, (ax) Trigeminal, (ay) Trochlear, (az) Tympanic, (ba) Vagus, (bb) Vestibulocochlear, (bc) Vidian's (Nerve of Pterygoid Canal), (bd) Zygomatic, (be) Zygomaticofacial, and (bf) Zygomaticotemporal.

As discussed above, the methods of the invention are performed intra-operatively, i.e., during a surgical procedure. The surgical procedure is any procedure that can be performed on a subject's head or neck. As used herein, the term "head" includes the face. For example, the surgical procedure can be the removal of tumors in the head and neck area, such as cerebellopontine-angle tumors. Other types of cancers in the head and neck area include Adenocystic carcinoma, Ameloblastoma, Esthesioneuroblastoma, Hurttle cell tumor, Mucoepidermoid carcinoma, Salivary duct tumor, and Thyroid cancer (e.g., papillary, follicular, anasplastic). The skilled artisan is well familiar with other types of head and neck cancers and tumors. Other exemplary surgical procedures include parotid-resection because of malignancy, proximal brachial plexus reconstruction, nerve harvesting for bypass grafting after nerve injury, carotid endarterectomy, cranial base dissections, sentinel lymph node biopsy, and isolation of nerves for iatrogenic injury in case of, for example, glossopharyngeal neuralgia. Yet other suitable surgical procedures include plastic and reconstructive surgery in the head and neck area. Such surgical procedures further include wrinkle removal (for example, Botox injection), face lifts, nose surgery (rhinoplasty), eyelid surgery (blepharoplasty), and many others that would be obvious to the skilled artisan.

In one embodiment, the surgical procedure requires or can be assisted by the location of sentinel lymph nodes in the subject's head or neck. For example, the surgical procedure can be sentinel lymph node biopsy. By way of background, cancerous growths and lymph nodes are commonly surgically removed in an attempt to arrest the spread of cancer in subjects. The sentinel lymph nodes are the lymph nodes most likely to receive lymphatic drainage from a tumor, and thus to contain the metastizing cancer before other lymph nodes. Sentinel lymph node mapping is a minimally invasive surgical procedure used to evaluate lymph nodes in the anatomical region surrounding a cancer. If cancer is found in the sentinel lymph nodes, additional lymph nodes are often removed from the subject. If no cancerous tissue is found in the sentinel lymph nodes, it becomes likely that cancer has not spread to other lymph nodes, and hence would suggest that removal of other lymph nodes is not necessary. It would thus be useful for the surgical team to be able to image the lymph nodes (and preferably the SLN) and the nerves in the vicinity of the lymph nodes when performing this procedure.

Thus, in certain embodiments of the invention, the method further includes the step of administering a second administration of a fluorescent dye to the subject. The second administration can be of the same or different fluorescent dye as in the first administration. This second administration is given to the subject between about 5 minutes and about 20 minutes before exposure to radiant energy as described herein. In other embodiments, acceptable time frames for the second administration include: between about 5 minutes and about 30 minutes, between about 5 minutes and about 40 minutes, between about 5 minutes and about 50 minutes, between about 5 minutes and about 60 minutes, between about 5 minutes and about 70 minutes, between about 5 minutes and about 80 minutes, between about 5 minutes and about 90 minutes, between about 5 minutes and about 120 minutes, between about 5 minutes and about 240 minutes, between about 5 minutes and about 360 minutes, between about 5 minutes and about 480 minutes, between about 5 minutes and about 600 minutes, between about 5 minutes and about 720 minutes, between about 5 minutes and about 960 minutes, between about 5 minutes and about 1080 minutes, between about 5 minutes and about 1200 minutes, between about 5 minutes and about 1320 minutes, and between about 5 minutes and about 1440 minutes before exposure to the radiant energy. The surgical team thus observes the one or more fluorescent images obtained as described herein to determine the location of the sentinel lymph node. They may search for the non-diffused ICG signature within the node(s) to determine the location of SLNs.

In yet other embodiments, both the SLNs and one or more nerves may be imaged in a subject even though the subject receives only a first administration of the fluorescent dye as described above. The skilled artisan will understand that the fluorescent dye will need to be administered so that there is sufficient time before the surgical procedure for the dye to be taken up by one or more nerves and SLNs. The skilled artisan will further understand that the imaging must take place while the fluorescent dye is visible in the one or more nerves and SLNs.

In another embodiment, the method further comprises administering a radioactive tracer, such as Technetium Tin or 99Tc-nanocolloid to the subject. The skilled artisan is familiar with the use of radioactive tracers in SLN biopsies to grossly determine the position of the lymph nodes by detecting the radiation from the radioisotope that spontaneously accumulates in the lymph nodes. In particular, the tumor site is often injected with a radioisotope that travels via the lymphatic channels to the sentinel lymph node. The sentinel lymph node then becomes radioactively visible, or "hot." Radioisotope detectors are able to identify or locate the radioactive lymph node through auditory and/or other signals. For example, Anja-A Dunne et al., Auris Nasus Laryn 28 (2001) 339-344, which is incorporated by reference herein in its entirety, describes an example of a methodology for use of radioisotopes. Other methods are well-known in the art.

In another embodiment, a radioisotope is not used. In this embodiment, the gross position of one or more lymph nodes is determined by observing the fluorescent image. Lymph nodes may be identified in the fluorescent image by their size, shape, gross position, and/or fluorescent dye signature.

The invention also contemplates obtaining a plurality of images. The plurality of images may be compared to each other to determine the effectiveness of a therapy, e.g. removal of sentinel lymph nodes or to confirm that a nerve has not been inadvertently cut or otherwise damaged.

Dyes

Suitable fluorescent dyes include any non-toxic dye that fluoresces when exposed to radiant energy, e.g. light. In certain embodiments the dye is a fluorescent dye that emits light in the infra red spectrum. In certain embodiments the dye is a tricarbocyanine dye such as indocyanine green (ICG). ICG can be purchased from Akorn, Inc. (Buffalo Grove, Ill.). In other embodiments the dye is selected from Fast-Blue, Evans-Blue, True Blue, Granular Blue, Fluoro-Gold, fluoresceine, Nuclear Yellow, Lucifer Yellow, Diamidino Yellow, Fluoro-Emerald. In yet other embodiments, the dye can be a carbocyanine dye, such as 1,1'-dioctadecyl-3,3,3',3'-tetramethylindo-carbocyanine perchlorate (DiI), fast DiI, 3,3'-dioctadecyloxacarbocyanine perchlorate (DiO), 4-(4-didecylaminostyryl)-N-methyl-pyridinnium iodide (DiAsp), 4-(4-dihexadecylaminostyryl)-N-methyl-pyridinium, and others. In yet other embodiments the dye is a fluorescently tagged dextran amine or a biotinylated dextran amine, such as Fluoro-Ruby, Mini Ruby, Texas Red, rhodamine-B dextran amine (RBD), a fluorescein conjugated dextran amine, etc. Other acceptable dyes include diamidinophenylindol (DAPI), choleratoxin subunit b (CTB), fluorescently tagged beads, rhodamine-isothiocyanate (RITC), plant lectins, horseradish perioxidase (HRP), wheat-germ agglutinin conjugated to HRP (WGA-HRP), propidium iodide (PI), a cyanate, a stilbidin-derivative, Cholera toxin B subunit (CTB), Phaseolus vulgaris leucoagglutinin (PHA-L), and diaminido yellow. Yet other suitable dyes will be obvious to the skilled artisan.

The aforementioned dyes may be mixed or combined in certain embodiments. In some embodiments dye analogs may be used. A dye analog includes a dye that has been chemically modified, but still retains its ability to fluoresce when exposed to radiant energy of an appropriate wavelength.

In some embodiments the dye may be administered parenterally, such as by subcutaneous or intramuscular injection e.g., as a bolus injection for each administration. Preferably, it is administered in or near the area where the surgical procedure is to be performed on the subject's body. In some embodiments the bolus injection may comprise a volume of about 0.5 ml. In other embodiments the bolus injection may comprise a volume in the range of about 0.01 µL to about 10 ml. In some embodiments the dye may be administered by a catheter, e.g. during a minimally invasive procedure. Where multiple dyes are used they may be administered simultaneously, e.g. in a single bolus, or sequentially, e.g. in separate boluses. Dye administration and neural transport thereof is discussed in Kobbert et al., *Progress in Neurobiology*, 62:327-351 (2000), and Schmued et al., *Brain Research* 526: 127-134 (1990), and Marangos et al., *Hearing Research*, 162: 48-52 (2001) which are hereby incorporated by reference in their entirety. Administration of fluorescent dye for imaging sentinel lymph nodes is described in U.S. Pat. No. 6,804,549 (Hayashi) and Nimura et al., *British Journal of Surgery*, 91:575-579 (2004), which are hereby incorporated by reference in their entirety.

In each administration, the dye may be administered at a suitable concentration such that the fluorescence may be detected when the appropriate wavelength of radiant energy is applied. In some embodiments where the dye is ICG, a suitable concentration is about 0.03 mg/ml at the site of detection. In other embodiments a suitable concentration of ICG is in the range of about 0.003 mg/ml to about 75 mg/ml. In some embodiments the ICG is administered in the range of about 1 mg/kg body weight to about 6 mg/kg body weight. In yet other embodiments the dye is administered at a concentration of about 0.5 mg/kg body weight. In still other embodiments the dye is administered in a range of about 0.01 mg/kg body weight to about 3 mg/kg body weight. In certain embodiments a suitable maximum daily dose of ICG may be administered to a subject. The maximum daily dose may be in the range of about 70 mg to about 140 mg.

The dye may be provided as a lyophilized powder or solid. In certain embodiments it may be provided in a vial, e.g. a sterile vial that may permit reconstitution with a sterile syringe. It may be reconstituted using any appropriate carrier or diluent. Examples of carriers and diluents are provided below. In certain embodiments the dye may be reconstituted at a concentration in the range of about 0.001 µg/µL to about 1000 µg/µL. For example, 250 µg of ICG in 50 µL glucosed water (concentration of 5 µg/µL) may be administered. In another example, 5 µg of ICG in 100 nL glucosed water (concentration of 50 µg/µL) may be administered. The dye may be reconstituted, e.g., with water or saline, immediately before administration.

Diluents and Carriers

Any diluent or carrier that will maintain the dye in solution may be used. As an example, in certain embodiments where the dye is ICG the dye may be reconstituted with water. In other embodiments where the dye is ICG, the dye may be reconstituted with an alcohol, e.g. ethyl alcohol. In some embodiments once the dye is reconstituted it may be mixed with additional diluents and carriers. In some embodiments the dye may be conjugated to another molecule, e.g., a protein, a peptide, an amino acid, a synthetic polymer, or a sugar, e.g., to enhance solubility or to enhance stability. In yet other embodiments, the dye may be combined with saline.

Additional examples of diluents and carriers which may be used in the invention include glycerin, polyethylene glycol, propylene glycol, polysorbate 80, Tweens, liposomes, amino acids, lecithin, dodecyl sulfate, phospholipids, deoxycholate, soybean oil, vegetable oil, safflower oil, sesame oil, peanut oil, cottonseed oil, sorbitol, acacia, aluminum monostearate, polypxylethylated fatty acids, and mixtures thereof. Additional buffering agents may optionally be added including Tris, HCl, NaOH, phosphate buffer, and HEPES.

Imaging Systems Useful to Carrying Out Methods

The skilled artisan is familiar with imaging systems for obtaining fluorescent images. For example, imaging techniques and systems using fluorescent dyes have been described for the heart and eye (see, U.S. Pat. Nos. 5,279,298 and 6,915,154; U.S. patent application Ser. No. 10/619,548 (published as US 2004-0206364 A1), all of which are incorporated herein by reference in their entirety. Similarly, Michel Paques et al. Arch Opthalmol, Vol 121, 367 (2003) describes systems and a procedure used to image nerves in the eyes of rats. This reference is hereby incorporated herein by reference in its entirety.

U.S. Pat. No. 6,804,549 (Hayashi) discloses systems suitable for imaging sentinel lymph nodes intra-operatively and is hereby incorporated by reference in its entirety. Nimura et al., *British Journal of Surgery*, 91:575-579 (2004) discloses methods and equipment used to image sentinel lymph nodes in the human breast, and is hereby incorporated by reference in its entirety.

Thus, the same or different systems may be used to image the nerves and sentinel lymph nodes in the head and neck within various embodiments of the invention. Preferably, the same system is used. In some embodiments, the parameters of the system may need to be fine-tuned by the user when switching between nerve imaging to SNL imaging. For example, the power of the laser and gain of the camera may need to be adjusted. It is believed that such fine-tuning adjustments are within the ability of the skilled artisan.

By way of example, an imaging system appropriate for use with the methods and kits described herein includes an energy source capable of emitting sufficient radiant energy such that the fluorescent dye fluoresces and an imaging member or sensor such as a camera for capturing a fluorescent image.

Radiant Energy

In certain embodiments of the invention, radiant energy is applied to the area of the head or neck for which an image is desired, in an amount sufficient to cause a fluorescent dye to fluoresce thereby permitting at least one nerve to be imaged. In another embodiment, radiant energy is applied in an amount sufficient to cause a fluorescent dye to fluoresce thereby permitting at least one lymph node to be imaged. In some embodiments the energy is light energy. In some embodiments the source of the light energy is a laser. An example of a suitable laser is the Magnum 3000 (Lasiris St-Laurent, Quebec, Canada), however, the skilled artisan will appreciate that many other suitable lasers are commercially available. The laser may be comprised of a driver and diode. The laser may optionally include a filter, e.g. a bandpass filter, to ensure that the emitted radiation is of a substantially uniform wavelength. The laser may comprise optics for diverging the laser. The optics may be adjustable permitting variation in the field of illumination. The adjustable optics may also be used to provide even illumination over a given area.

In some embodiments the laser output is continuous. In other embodiments the laser output is pulsed. The pulsed output may be synchronized with image acquisition by using a pulse generator. In some embodiments the laser pulse may last for at least 3 femtoseconds. In some embodiments the laser output lasts for about 30 seconds. In other embodiments the laser output lasts about 0.5 seconds-about 60 seconds. A suitable repetition rate for the pulsed laser may be in the range of e.g., 1 Hz-80 MHz, 10 Hz-100 Hz, 100 Hz-1 kHz, 1 kHz-100 kHz, 100 kHz-80 MHz. In some embodiments the laser may be operated at power output of 2.2 watts. In other embodiments the laser may be operated at power output in the range of 1-4 watts. In still other embodiments the average power is less than 10 watts.

In some embodiments the source of the light energy is an incandescent light with an appropriate filter so as to provide a suitable wavelength of light to induce the fluorescent dye to fluoresce. In yet other embodiments the light source is light emitting diode (LED) or an array of light emitting diodes.

In some embodiments the light energy may have a wavelength in the range of 150 nm-1500 nm. In other embodiments the light energy may be comprised of infra red light. In some embodiments the administered light has a wavelength of about 805 nm. In other embodiments the administered light has a wavelength in the range of about 800 to about 850 nm, and preferably in the range of about 805 nm-about 850 nm. The light energy may be administered at a wavelength that is shorter than the collection wavelength, i.e. detection wavelength. The light energy may be administered diffusely so as not to damage the irradiated tissue. In some embodiments the light is administered over an area of about 7.5 cm×7.5 cm. In other embodiments the light is administered over an area in the range of about 1 cm×1 cm to about or 30 cm×30 cm. In other embodiments, the area is larger than about 30 cm×30 cm.

In some embodiments the system comprises a sterile drape. The sterile drape covers all or part of the system to prevent or minimize the risk of contamination of the subject. The sterile drape may have an aperture in it. The aperture may be covered with a material which is capable of transmitting radiant energy, e.g., infra red light generated by a laser.

Image Acquisition

Image acquisition may be achieved using any sensor capable of detecting a fluorescent signal. Examples include silicon based sensors, composite metal oxide semi oxide (CMOS) sensors and photographic film. In one embodiment the sensor comprises a camera, e.g. charge coupled device (CCD). Examples of a CCD include the Hitachi KP-M2; KP-M3 (Hitachi, Tokyo, Japan).

In certain embodiments an endoscope comprising a sensor may be used. The endoscope may additionally comprise a source of radiant energy. The endoscope may be comprised of optical fibers. In certain other embodiments a microscope comprising a sensor may be used, e.g., a surgical microscope. In another embodiment the sensor comprises a video camera.

In certain embodiments the sensor may capture images at the rate of at least 10 per second, at least 15 per second, at least 20 per second, at least 30 per second, at least 50 per second. Thus in certain embodiments the invention contemplates a plurality of images. In other embodiments the invention contemplates one image.

The camera may be comprised of a means for focusing the image, such as a manual means or automated means for focusing an image. The camera may further be comprised of a lens system that permits magnification of an image field.

In one embodiment the relative positioning of the camera and laser is fixed so as to enhance clarity and minimize background noise. In this embodiment the laser is located at an angle of less than about 85° with respect to the axes of the laser and the camera. In another embodiment the laser is located at an angle from about 20° to about 70° with respect to the axes of the laser and the camera.

In certain embodiments the camera relays the captured image to an analog to digital converter and then through image capture and/or processing software running on a computer. The digital image of the fluorescing agent, corresponding to a lymph node and/or nerve may then be displayed on a monitor and recorded by a computer or a peripheral device. The image may be stored in any suitable medium, e.g., a hard drive, an optical disk, magnetic tape. In certain embodiments the computer is a personal computer comprising at least 512 Megabytes of RAM and at least 10 Gigabytes of storage. In some embodiments the computer may contain a Pentium IV processor (Intel, Santa Clara, Calif.). In some embodiments the computer may also have a CD and DVD drive. The drive may have read and write functionality.

FIG. 1 illustrates a flowchart of software that may be used within the scope of the present invention. The skilled artisan will understand that such software includes instructions stored on computer-readable medium. When executed, the software program provides instructions to the computer processor as described below. The skilled artisan will further understand that the computer is in communication with the laser, sensor and display as described herein.

At start (step 10) the user may be presented with multiple dialog boxes or other common user interface paradigms. For example, the user may be queried about whether he wishes to start a new study (step 20). If the user indicates that he does, he may be instructed to input or otherwise selects a patient for the study. For example, the user may be prompted to choose a name from a list linked to a database that is accessible to the computer. Alternately, he may be prompted to input a patient identifier. The computer may then access the database to determine the existence of additional information associated with the patient, and preferably to obtain such information. In a preferred embodiment, the software requires the user to input or otherwise select values for Patient First Name, Last Name and ID number fields. Most preferably, sufficient information is inputted or otherwise loaded so that images may be stored according to the Digital Imaging and Communications in Medicine (DICOM) standard. The DICOM Standard is a product of the DICOM Standards Committee and its many international working groups. Day-to-day operations are managed by the National Electrical Manufacturers Association (Rosslyn, Va.). The standard is publicly available at the website http://medical-.nema.org/, and is incorporated herein by reference in its entirety.

After patient data is inputted (step 30), the monitor or other display displays images captured by the camera or other sensor in communication with the computer (step 40). At this point, the user can change the position, orientation, gain or other parameter of the camera to obtain a desired view of the patient.

Alternately, the user may choose to continue a study (step 25) at start 10. Upon such indication, the process proceeds to step 40.

Once the image is displayed, the user is prompted to indicate whether he wishes to copy sequences (step 35) or acquire sequence (step 50). The term "sequences" refers to data associated with real-time images captured by a camera or other sensor in communication with the computer. Once the user indicates that he wants to acquire images from the sensor in step 50, the computer causes the laser to turn on (step 60), and it stores the video sequence obtained from the sensor in RAM (step 70). Real time images continue to be displayed on the display. The user is then queried about whether he wishes to turn the laser off (step 80). If he indicates that he does, the computer causes the laser to shut off (step 95). Alternately, if the user does not indicate that he wants to shut off the laser, the computer determines whether a pre-determined amount of time (e.g., 34 seconds) has elapsed from step 60. Once that pre-determined amount of time has elapsed, the computer causes the laser to shut off. The video sequences continue to be stored in RAM until the laser is turned off. Once the laser is turned off, the user is queried as to whether he wishes to save the sequence (step 105). If he indicates in the affirmative, then the sequences are stored to hard drive (step 115) or other media.

Returning now to step 40 for purposes of describing the software, once the real time image is displayed, the user is queried as to whether he wishes to copy sequences (step 35). If the user indicates that he does, the images associated with the study are selected (step 45) and burned on compact disk or other selected media (step 55). Alternately, the software may allow the user to select specific images for storage on selected media (step 45). Preferably, the image(s) are stored in a format that is compatible with a picture archiving and computer system, for example in a DICOM format.

In another embodiment, the camera may also direct images to a television/VCR system such that the image(s) may be displayed in real time and/or recorded and played back at a later time. Since the image(s) may be used to guide all or part of the surgical procedure, the image(s) may be displayed through out the length of the surgical procedure. In other embodiments, the image(s) may be displayed for less than the entire length of the surgical procedure. In another embodiment the software permits manipulating the images after acquisition, such as zooming, region of interest selection, change of brightness and contrast, and displaying multiple images simultaneously.

Kits of the Invention

Certain embodiments of the invention provide a kit for reducing the risk of iatrogenic nerve injury to a subject during a surgical procedure of the head or neck. The kit includes a first fluorescent dyes (as described above) in a total of one or more sterile containers, and instructions for using said one or more fluorescent dyes according to any of the methods of the invention. The sterile container(s) may be hermetically sealed and comprised of a rubber septum. The containers may be sized to receive a predetermined volume of one or more fluorescent dyes, diluents or carriers. As described above, the fluorescent dye may be in a lyophilized solid or in liquid form.

In certain embodiments, the instructions instruct that the first fluorescent dye should be administered to a subject. The instructions further instruct (a) the application of a sufficient amount of energy to the subject's head or neck such that the fluorescent dye fluoresces, (b) intra-operatively obtaining a fluorescent image of at least a portion of the subject's head or neck, and (c) observing the fluorescent image to determine the presence or absence of at least one nerve in the fluorescent image. As described above in reference to the methods of the invention, in certain embodiments, the instructions further instruct the administration of the first fluorescent dye at least one hour before the surgical procedure, and at least one day before the surgical procedure in another embodiment. Other acceptable times for administrations within the scope of the invention are further described above.

As further described above, the surgical procedure may be any surgical procedure listed herein.

In some other embodiments, a second fluorescent dye is included in the kit. For example, a second fluorescent dye may be useful when the surgical procedure is sentinel lymph node biopsy as described above.

The instructions may be disseminated in virtually any way that information is disseminated. For example, they may be in written, electronic, or other form. They may be included with the kit, such as on computer-readable media or on a paper insert, or otherwise made available separately (e.g., via e-mail, by facsimile, in a catalog, on a website, orally, etc.)

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

The invention claimed is:

1. An intra-operative method for determining the location of a nerve to reduce the risk of iatrogenic nerve injury to a subject during a surgical procedure of the subject's head or neck, comprising:
   a. administering a first fluorescent dye to the subject;
   b. applying an amount of energy to the subject's head or neck such that the fluorescent dye fluoresces;
   c. intra-operatively obtaining a fluorescence image of at least a portion of at least one nerve in the subject's head or neck by identifying the at least one nerve from the fluorescence of the fluorescent dye;
   d. determining the location of the at least one nerve in the fluorescence image; and
   e. proceeding with the surgical procedure, in view of the determination of the location of the at least one nerve in the fluorescence image, in a manner that reduces the risk of iatrogenic nerve injury.

2. The method of claim 1, wherein the subject is a human.

3. The method of claim 1, wherein the first fluorescent dye is administered to the subject at least one hour before applying the energy to the subject's head or neck such that the fluorescent dye fluoresces.

4. The method of claim 3, wherein the first fluorescent dye is administered to the subject at least one day before applying the energy to the subject's head or neck such that the fluorescent dye fluoresces.

5. The method of claim 1, wherein the first fluorescent dye is a tricarbocyanine dye or an analog thereof.

6. The method of claim 5, wherein the tricarbocyanine dye is indocyanine green.

7. The method of claim 1, wherein the first fluorescent dye is administered parenterally.

8. The method of claim 1, wherein the first fluorescent dye is administered as a bolus injection.

9. The method of claim 1, wherein the energy is light energy.

10. The method of claim 1, wherein the wavelength of the light energy is in the infra-red spectrum.

11. The method of claim 10, wherein the wavelength of the light energy is about 805 nanometers.

12. The method of claim 1, wherein the image is obtained by camera.

13. The method of claim 12, wherein the camera is a video recorder.

14. The method of claim 13, wherein the camera is a charge coupled device.

15. The method of claim 1, further comprising using an endoscope comprising a sensor to obtain the fluorescence image.

16. The method of claim 1, further comprising using a microscope comprising a sensor to obtain the fluorescence image.

17. The method of claim 1, wherein the surgical procedure is removal of a tumor from the head or neck.

18. The method of claim 1, wherein the surgical procedure is selected from the group consisting of:
   a. removal of a cerebellopontine-angle tumor;
   b. removal of an adenocystic carcinoma tumor;
   c. removal of an ameloblastoma tumor;
   d. removal of an esthesioneuroblastoma tumor;
   e. removal of a Hurttle cell tumor;

f. removal of a Mucoepidermoid carcinoma tumor;
g. removal of a salivary duct tumor;
h. removal of a thyroid cancer tumor;
i. acoustic-neuroma surgery;
j. parotid-resection;
k. proximal brachial plexus reconstruction;
l. nerve harvesting for bypass grafting after nerve injury;
m. carotid endarterectomy;
n. cranial base dissections;
o. isolation of nerves for iatrogenic injury;
p. plastic surgery in the head or neck;
q. reconstructive surgery in the head or neck; and
r. sentinel lymph node biopsy.

19. The method of claim 1, further comprising administering a second fluorescent dye to the subject.

20. The method of claim 19, wherein the first fluorescent dye is the same dye as the second fluorescent dye.

21. The method of claim 19, wherein the second fluorescent dye is a different dye than the first fluorescent dye.

22. The method of claim 19, wherein the second fluorescent dye is administered between about 5 and about 20 minutes before applying the energy to the subject's head or neck such that the fluorescent dye fluoresces.

* * * * *